United States Patent
Fonash et al.

(10) Patent No.: US 7,122,790 B2
(45) Date of Patent: Oct. 17, 2006

(54) MATRIX-FREE DESORPTION IONIZATION MASS SPECTROMETRY USING TAILORED MORPHOLOGY LAYER DEVICES

(75) Inventors: Stephen J. Fonash, State College, PA (US); Ali Kaan Kalkan, State College, PA (US); Joseph Cuiffi, State College, PA (US); Daniel J. Hayes, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 35 days.

(21) Appl. No.: 10/144,456

(22) Filed: May 13, 2002

(65) Prior Publication Data

US 2002/0187312 A1 Dec. 12, 2002

Related U.S. Application Data

(63) Continuation-in-part of application No. 09/580,105, filed on May 30, 2000, now Pat. No. 6,399,177.

(60) Provisional application No. 60/290,876, filed on May 14, 2001.

(51) Int. Cl.
 *B01D 59/44* (2006.01)
(52) U.S. Cl. .................. 250/288; 436/174; 436/149
(58) Field of Classification Search ............... 250/423, 250/281, 282, 284, 287, 288, 425, 423 P, 250/423 R, 423 F, 424, 426, 427; 427/527, 427/579; 428/119, 469
 See application file for complete search history.

(56) References Cited

U.S. PATENT DOCUMENTS

| | | | | |
|---|---|---|---|---|
| 4,728,796 A * | 3/1988 | Brown | ................... | 250/423 P |
| 4,988,879 A * | 1/1991 | Zare et al. | ................ | 250/423 P |
| 5,260,571 A | 11/1993 | Cottrell et al. | ............... | 250/288 |
| 5,382,793 A * | 1/1995 | Weinberger et al. | ........ | 250/288 |
| 5,389,786 A * | 2/1995 | Itoh et al. | .................... | 250/307 |
| 5,552,272 A | 9/1996 | Bogart | .......................... | 435/6 |
| 5,580,733 A * | 12/1996 | Levis et al. | ..................... | 435/6 |
| 5,589,685 A * | 12/1996 | Jen Wu et al. | .............. | 250/282 |
| 5,719,060 A * | 2/1998 | Hutchens et al. | ........... | 436/174 |
| 5,770,272 A * | 6/1998 | Biemann et al. | ............ | 427/421 |
| 5,777,324 A * | 7/1998 | Hillenkamp | ................. | 250/288 |
| 5,828,063 A * | 10/1998 | Koster et al. | ................ | 250/288 |
| 5,854,486 A * | 12/1998 | Dreyfus | ...................... | 250/288 |
| 5,882,496 A | 3/1999 | Northrup et al. | ........... | 204/601 |
| 5,894,063 A | 4/1999 | Hutchens et al. | ........... | 436/155 |
| 5,919,712 A * | 7/1999 | Herron et al. | ............... | 436/518 |
| 6,057,543 A * | 5/2000 | Vestal et al. | ................. | 250/282 |
| 6,071,610 A * | 6/2000 | Jarrell et al. | ................. | 428/335 |
| 6,288,390 B1 * | 9/2001 | Siuzdak et al. | ............. | 250/288 |
| 6,399,177 B1 * | 6/2002 | Fonash et al. | ............... | 428/119 |

(Continued)

OTHER PUBLICATIONS

Cuiffi, "Desorption-Ionization mass spectrometry using deposited nanostructured silicon films," Anal. Chem. vol. 73, No. 6, Mar. 15, 2001, 1292-1295.

(Continued)

*Primary Examiner*—David A. Vanore
(74) *Attorney, Agent, or Firm*—Burns & Levinson LLP; Orlando Lopez; Peter J. Borghetti

(57) ABSTRACT

There is disclosed an apparatus for providing an ionized analyte for mass analysis by photon desorption comprising at least one layer for contacting an analyte, and a substrate on which said layer is deposited. Upon irradiation of said apparatus, said analyte desorbs and ionizes for analysis by mass spectrometry. The layer or layers of said apparatus comprise a continuous film, a discontinuous film or any combinations thereof.

67 Claims, 7 Drawing Sheets

U.S. PATENT DOCUMENTS 6,454,924 B1 * 9/2002 Jedrzejewski et al. ...... 204/601
2002/0193950 A1 * 12/2002 Gavin et al. .................. 702/28

OTHER PUBLICATIONS

Dale et al. "Graphite/Liquid mixed matrices for laser desorption/ionization mass spectrometry." Anal. Chem. vol. 68, No. 19, Oct. 1, 1996, 3321-3329.

Kruse et al. "Experimental factors controlling analyte ion generation in laser desorption/ionization mass spectrometry on porous silicon." Anal. Chem. vol. 73, No. 15, Aug. 1, 2001, 3639-3645.

Shen et al. "Porous Silicon as a versatile platform for laser desorption/ionization mass spectrometry." Anal. Chem., vol. 73, No. 3, Feb. 1, 2001, 612-619.

Wei et al. "Desorption-ionization mass spectrometry on porous silicon." Nature. vol. 399, May 20, 1999, 243-246.

Zhan et al. "Laser desorption substrate effects." J. Am. Soc. Mass Spectrom. 1997, 8. 525-531.

* cited by examiner

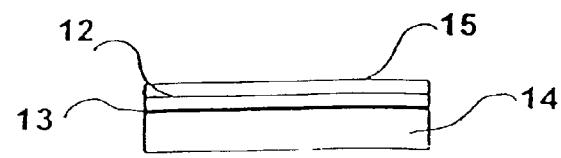
Fig. 5a                     Fig. 5b
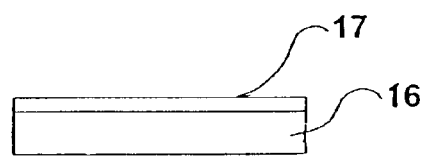
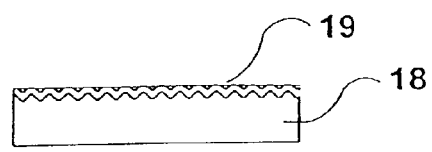
Fig. 5c                     Fig. 5d
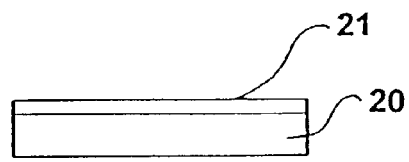
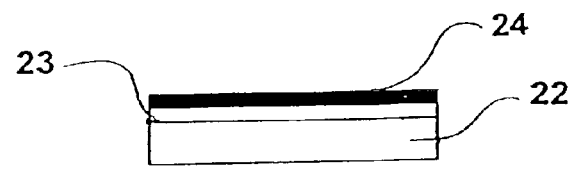
Fig. 5e                     Fig. 5f

MATRIX-FREE DESORPTION IONIZATION MASS SPECTROMETRY USING TAILORED MORPHOLOGY LAYER DEVICES

This application claims priority from U.S. Provisional Application No. 60/290,876, filed May 14, 2001, and is a continuation in part application of U.S. application Ser. No. 09/580,105, filed May 30, 2000 now U.S. Pat. No. 6,399,177. This application also claims priority from U.S. patent application Ser. No. 10/104,749, filed Mar. 22, 2002, which is a continuation of U.S. patent application Ser. No. 09/580,105, filed May 30, 2000. Priority is also claimed from U.S. application Ser. No. 09/836,449, filed Apr. 17, 2001, which is a continuation in part of U.S. patent application Ser. No. 09/739,940, filed Dec. 19, 2000, which is a continuation in part of U.S. patent application Ser. No. 09/580,105, filed May 30, 2000.

BACKGROUND OF THE INVENTION

1. Field of the Invention

The present invention relates to tailored-morphology material systems and their use in molecular mass analysis by electromagnetic energy desorption-ionization mass spectrometry. Areas of interest for this technology include, but are not limited to, chemical research and manufacturing, pharmaceutical research and manufacturing, bio-medical research and screening, head-space and environmental monitoring, and other applications involving molecular analysis.

2. Description of the Prior Art

Light desorption-ionization mass spectrometry is a very common and powerful technique for mass analysis of molecules. It is a technique which can be broadened to include the whole spectrum of electromagnetic energy for the desorption-ionization step. However, with recent demands in throughput and small molecule screening, the most popular and widely used laser-based technique, known as MALDI (matrix-assisted laser desorption-ionization), has limitations. MALDI was developed in the mid-eighties and is still being refined today for the analysis of a wide range of compounds with emphasis on proteins, peptides and other molecules in the range of 500–200,000 amu. In MALDI, the analyte (the molecules or compounds to be analyzed) is mixed in with an organic UV absorbent "matrix". This matrix provides a "soft" method of desorbing large molecules by allowing excess energy in the analyte to be transferred to the matrix molecules during the desorption process. The matrix also provides an environment suitable for the protonation of the analyte molecules, giving them a single, positively charged state. However, for small molecules (approximately 500 amu and below, such as drug molecules), the matrix molecules themselves provide background in the signal and complicate spectrum analysis. Furthermore, with modern demands in automation, throughput and reproducibility, the addition of the matrix to the analyte and its preparation become issues particularly in the case of throughput. These limitations were recognized during the onset of MALDI, leading to the study of non-matrix methods.

The first studies in matrix-less light desorption from a surface used metals and glasses as a media to immobilize the analyte molecules. These materials had non-textured morphologies, i.e., essentially they were non-porous and had a flat (continuous) surface. In a study using this approach, two incident light beams were used, one to desorb and one to ionize the molecules. Zhan, Q. et al., Amer. Soc. Mass Spectrom. 8, 525–531 (1997). This approach is termed two-photon ionization. Other similar methods used ion beams and thermal sources for these tasks. Problems with all these matrix-less light desorption techniques reported in the literature include a high degree of molecular fragmentation and a very limited mass range. These studies, and recent comments, maintain that smooth (non-porous) surfaces do not work effectively for matrix-less laser mass desorption. (See for example, Wei, J., et al., Nature. 399, 243–246 (1999). A recent report supports the understanding that smooth surfaces do not function effectively for matrix-less laser mass desorption. Kruse, R., et al., Anal. Chem. 73, 3639–3645, 2001.

It has been shown that matrix-less laser mass desoroption could be effective if done on a textured surface created with the use of electrochemically etched porous silicon. Wei, J., et al., Nature. 399, 243–246 (1999). With this material as a substrate for laser desorption ionization, significant improvement in non-matrix techniques for molecular analysis has been reported. Also, it was reported that electrochemically etched porous silicon provided mass detection in the range of 0–8000 amu with little fragmentation and little low mass noise. However, other results using this material raised concerns about the low mass collection of hydrocarbons and other contaminants leading to "dirty" low mass signals. Shen, Z., et al., *Anal. Chem.* 73, 612–619 (2001). The use of HOME-HF electrochemically etched Si, GaAs and GaN, which requires metallic patterning and a wet etching step leading to a porous microstructure, has also been reported for matrix-less laser mass desorption. Kruse, R., et al., Anal. Chem. 73, 3639–3645, 2001.

Further limitations of the electrochemically etched materials are their limited useful lifetimes for mass desorption-ionization applications (<3 weeks) which occur for these materials because of etchants trapped in the material during its manufacturing process. The processing of these etching approaches involves the galvanic etching of a crystal conductive substrate in a hydrofluoric acid based solution. Although the fundamental theory of the mechanism of desorption-ionization of molecules using these techniques is currently under investigation, research groups using these materials reported the importance of the porous structure to the success of mass desoprtion-ionization and reported that solid, smooth (i.e., non-textured) silicon and silicon dioxide coated silicon did not generate ion signals; i.e., were not useful for light desorbed mass spectroscopy.

In other work, liquid matrix materials combined with UV light adsorbing particles have been used in recent laser desorbtion/ionization experiments as an alternative to traditional MALDI matrix materials. Dale et al, Anal Chem, 68, 3321–3329 (1996) used a glycerol/graphite slurry to desorb detect proteins and peptides. This methodology proved less efficient in ionization than traditional MALDI and provided a very noisy spectrum from the glycerol contamination.

The use of a new material, deposited column/void network silicon, for laser desorption-ionization has eliminated several disadvantages associated with electrochemically etched material approaches. Cuiffi, J., et al., *Anal. Chem.* 73, 1293–1295 (2001). This reported technique of using deposited column/void network materials for mass desorption-ionization produced similar mass ranges and sensitivity to electrochemically etched material, but the film itself did not degrade over time. Furthermore the manufacturability of a deposited film system offers several advantages in cost, production throughput, contamination control, uniformity, and signal reproducibility. This deposited material also offers the further unique feature of having the capability to be deposited on a number of inexpensive substrates, including bio-degradable materials, plastics, and glass. On the other hand, electrochemically etched material always must be on a conducting substrate. In addition, Cuiffi et al. reported, for the first time, that solid (continuous) films of crystalline silicon and thermal silicon dioxide coated crystal silicon did give effective mass desorption-ionization spectroscopy signals. Cuiffi, J., et al., *Anal. Chem.* 73, 1293–1295 (2001).

The material systems of the present invention consist of one or more deposited film layers and a substrate on which they are deposited. The material system could also be grown (e.g., Si, SiGe alloy, Ge wafer materials) or casted (Si, SiGe, Ge sheet materials) and also function as the substrate. Unlike the previously reported techniques, our deposited material systems offer the flexibility of a number of deposition methods and encompass a broad range of material and morphological choices. These material systems can be uniquely tailored for mass spectrometry applications through choice of the substrate, deposition techniques and materials, deposition parameters and pre- or post deposition physical and chemical modification, which are unavailable in the techniques of electrochemically etched porous silicon whether used with one or two-photon ionization. Specifically, the substrate materials available with our technique are chosen from a group consisting of polymers, plastics, bio-degradable materials, semiconductors, metals, ceramics, insulators, glasses or combinations thereof. Electrochemically or HOME-HF etched porous materials require a conducting semiconductor substrate, and are fundamentally based on a subtractive electric current-driven etching process.

The materials of the present invention can be deposited. This can be done by one or a combination of the additive process comprising physical vapor deposition, chemical vapor deposition, molecular beam epitaxy, plasma assisted physical vapor deposition, plasma enhanced chemical vapor deposition, sol-gel, molecular self-assembly, electroplating, tape casting, spin casting, casting, liquid deposition, or assembly from liquid chemical precursors. The morphology of these materials, which is determined by the production technique and parameters, are application-specific and can range from a continuous (void free) solid with no surface texturing to high surface area to volume ratio (i.e., the deposited column-void nanotextured silicon film), or any intermediate morphologies.

The material systems of the present invention can also be altered by pre or post deposition physical or chemical modifications, which affect the morphology, surface chemistries and bulk material chemistries of the films.

Given these advantages, our material systems are easily integrated, when compared to other matrix-less light desorption/ionization techniques, with microelectronics, microfluidics and other micro and nanofabricated sensing devices.

Matrix free desorption/ionization mass spectrometry available using the tailorable morphology of our materials, has a variety of applications. The flexible nature of the substrate material composition, film composition, or both, permitted in our approach allows this technology to be used in atmospheric and reduced pressure desorption and ionization systems as a disposable consumable or reusable target. The composition and methods of production utilized in this technique allow for easy integration with microfabrication processes and microelectronic devices, such as microfluidics, microarrays, CMOS technology and thin film transistors. The matrix less desorption and ionization makes automated, high throughput sample analysis an attractive use of this technique.

The present invention presents a variety of structures that further expand the possibilities of molecular detection using light desorption-ionization, by providing low-cost, easily manufactured, tailorable material systems and techniques.

SUMMARY OF THE INVENTION

The present invention is directed to a class of layered structures comprising one or more layers, with tailored application-specific morphology, for use in light desorption-ionization mass spectrometry. This class of structures holds analytes and allows them to be desorbed and ionized in the presence of a light source for subsequent mass analysis. Analytes are preferably in an amount less than one millimole. Analyte is selected from the group consisting of organic chemical compositions, inorganic chemical compositions, biochemical compositions, cells, micro-organisms, peptides, polypeptides, proteins, lipids, carbohydrates, drug candidate molecules, drug molecules, drug metabolites, combinatorial chemistry products, nucleic acids, and any combinations thereof.

In order to perform [these two] the functions of desorption and ionization, the film structure and substrate of this invention must (1) effectively couple and absorb the incident electromagnetic energy (e.g., light), (2) transfer the energy from the incident energy into the analyte for desorption/ionization, and (3) provide the necessary surface and surroundings for the analytes to be desorbed and ionized. The structures of this invention may also be patterned or textured for tasks including increasing the surface area, enhancing ionization, enhancing optical absorption, and localizing the analyte. Also, chemical additives to the deposited films or analyte solution may also be used to enhance ionization and analyte detection. Finally, these material systems can be easily integrated with macro-scale and micro-scale devices. These aspects are explained and further detailed below. The class of structures of the present invention encompasses devices with one or more deposited films and a substrate to which they are adhered. The class of structures of this invention also encompasses structures with one or more layers from grown or caste materials.

Each layer in the device, including the substrate may perform one or more tasks. Two necessary tasks are the absorption of the light (done by the "absorption layer") and holding of the analyte (done by the "immobilization layer"). Other tasks may include enhancing optical coupling of the light into the absorber via increasing optical path length and/or optical impedance matching, enhancing thermal energy transfer into the analyte via high thermal conductivity, controlling drop drying and crystallization and providing a source of ionizing or ionizing enhancing reagents. A layer may also be present to apply a bias to the analyte-bearing layer during the light impingement step.

The present invention discloses an apparatus for providing an ionized analyte for mass analysis by light desorption mass spectrometry comprising at least one layer for contacting an analyte, and a substrate on which said layer is deposited, wherein said analyte upon irradiation of said apparatus with a light source desorbs and ionizes for analysis by mass spectrometry. The substrate is selected from the group consisting of semiconductors, glasses, plastics, polymers, biodegradable or biocompatible materials, metals, ceramics, insulators, organic materials, and any combinations thereof. At least one layer is selected from the group consisting of metals, semiconductors, insulators, ceramics, polymers, organic materials, inorganic materials, and any combinations thereof. At least one layer may be a continuous (non-textured) film, a textured (columnar or columnar-void) film, or any combinations thereof, and is deposited by physical vapor deposition, chemical vapor deposition, liquid deposition, molecular beam epitaxy, plasma assisted chemical vapor deposition, sol-gels, nebulization, electroplating, tape casting, spin coating, self-assembly, assembly from liquid chemical precursors, printing, and any combinations thereof.

The present invention also discloses a method for providing an ionized analyte for analysis of mass comprising providing an apparatus comprising at least one layer for contacting an analyte wherein said layer is deposited on a substrate, contacting an amount of an analyte containing entities such as molecules whose mass or masses are to be determined with said deposited layer, and irradiating said apparatus to desorb and ionize said analyte. Also, the present invention discloses a method for determining a physical property of an analyte component comprising providing an apparatus comprising at least one layer for contacting an analyte and a substrate on which said layer is deposited; positioning an amount of an analyte on the layer used for contacting an analyte of said apparatus; irradiating said apparatus having said contacted analyte; desorbing and ionizing at least one component of said analyte; and analyzing said ionized analyte component for a physical property, preferably mass to charge ratio of the ionized analylte.

BRIEF DESCRIPTION OF THE DRAWINGS

FIGS. 5a–f show various material system embodiments of the present invention.

DETAILED DESCRIPTION OF THE INVENTION

Figure 1:
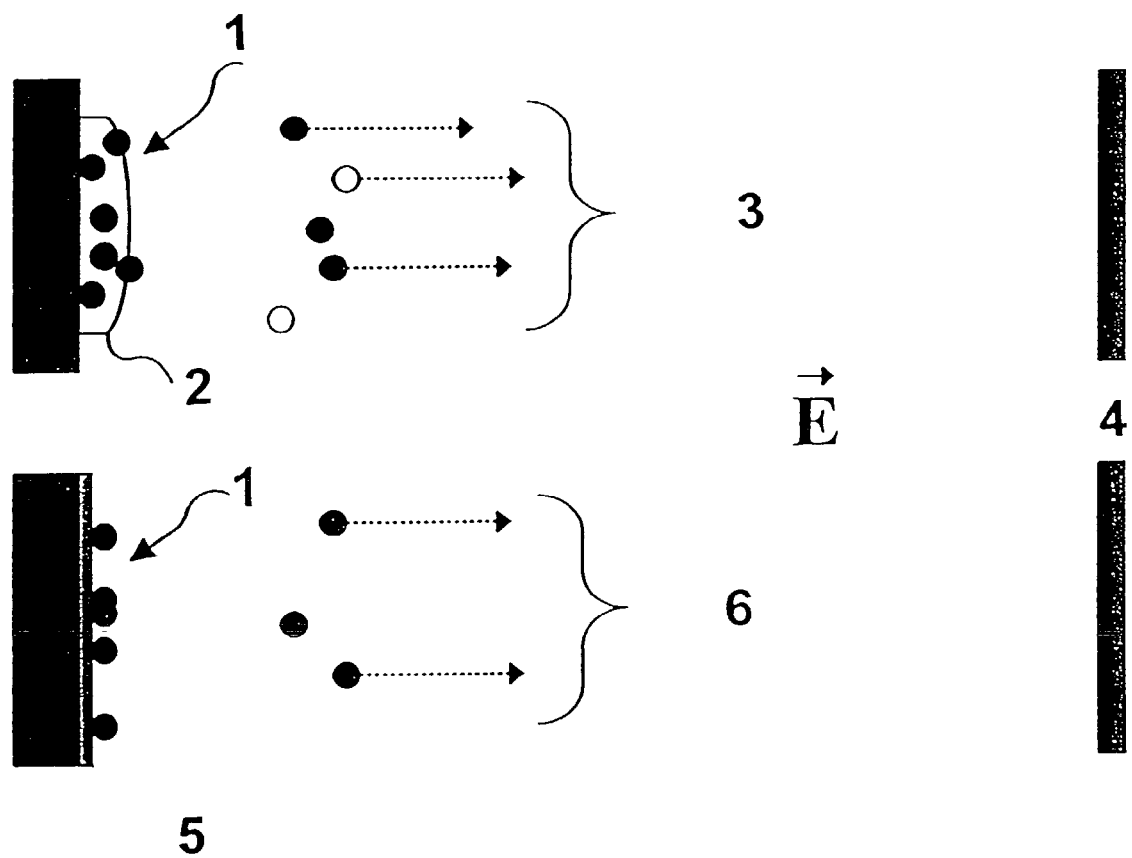
FIG. 1 is a schematic representation of the difference between MALDI (top) and the method of the present invention (bottom).

Referring now to FIG. 1, there is shown a schematic representation of the MALDI and the method of the present invention. Ultra-violet light (337 nm) 1 impinges matrix 2 to provide sample and matrix ions and neutrals 3 to reach detector 4.

Referring now to FIG. 5 which shows devices of various materials, FIG. 5a shows a device having a high surface area to volume ratio film or layer of columnar silicon 11 on a plastic substrate 10. The functions of the columnar silicon layer 11 are absorption, optical coupling, and immobilization. Advantages of this device include, but are not limited to, one-step production, inexpensive substrate material, and high molecular immobilization.

FIG. 5b shows a device having a layer of silicon dioxide 15 on a layer of amorphous silicon 12, on a layer of metal 13, on a glass substrate 14. The function of the amorphous silicon layer 12 is light absorption. The metal 13 and silicon dioxide 15 provide optical coupling; also, the silicon dioxide layer 15 provides immobilization. Advantages of this device are that it is reusable and provides little low mass noise.

FIG. 5c shows a device having a layer of silicon dioxide 17 on a substrate of crystal silicon 16. The function of the crystal silicon substrate 16 is light absorption. The functions of the silicon dioxide layer 17 are optical coupling and immobilization.

FIG. 5d shows a device having a layer of amorphous silicon 19 on a textured plastic substrate 18. The functions of the amorphous silicon layer 19 are light absorption and analyte immobilization. The function of the textured plastic substrate 18 is optical coupling.

FIG. 5e shows a device having a layer of amorphous silicon 21 on a glass substrate 20. The functions of the amorphous silicon layer 21 are light absorption and analyte immobilization. Neither the glass substrate 20 nor the amorphous silicon layer 21 provides optical coupling. The advantages of this device include, but are not limited to, one-step production of manufacture, and low mass noise.

FIG. 5f shows a device having a high surface area to volume ratio silicon dioxide (porous $SiO_2$) layer 24 on a layer of amorphous silicon 23 on a glass substrate 22. The device is preferably illuminated from below, i.e., from the glass substrate layer 22. The function of the amorphous silicon layer 23 is light absorption of the back illumination. The function of the porous $SiO_2$ layer 24 is analyte immobilization. The function of the glass substrate layer 22 is optical coupling. Advantages of this device include, but are not limited to, elimination of direct light exposure of the anlyte by providing illumination from below, and high molecular immobilization.

Figure 6:
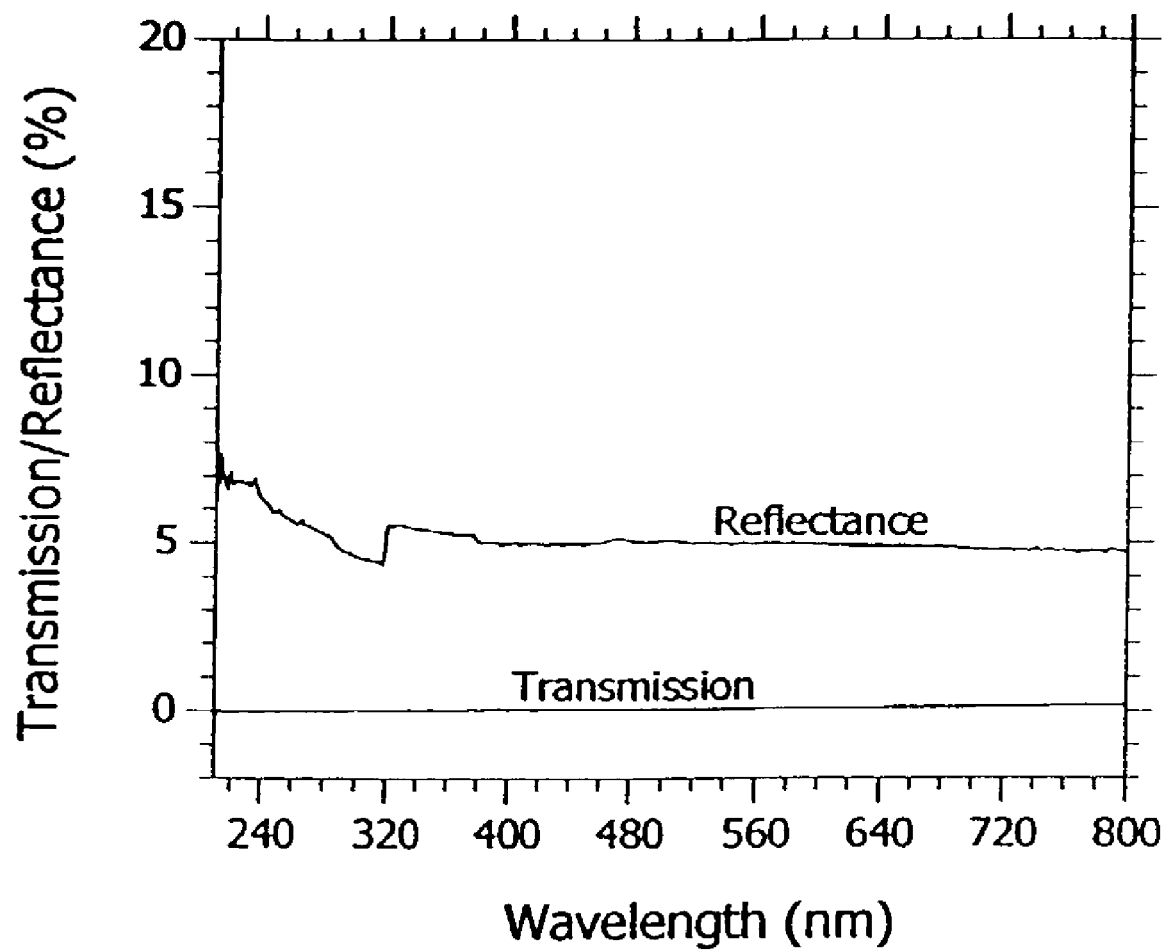
FIG. 6 Transmission and reflectance spectra of the Halogenated acidic polymer—carbon black composite film. Reflectance is with respect to barium sulfate.

FIG. 6 is a graphic representation of transmission and reflectance spectra a halogenated acid polymer—carbon black composite film of the present invention. Reflectance is with respect to barium sulfate. Exceptionally low reflectance and almost no transmission indicated that the composite film absorbs most of the light impinging on it in the visible and ultraviolet range.

Figure 7:
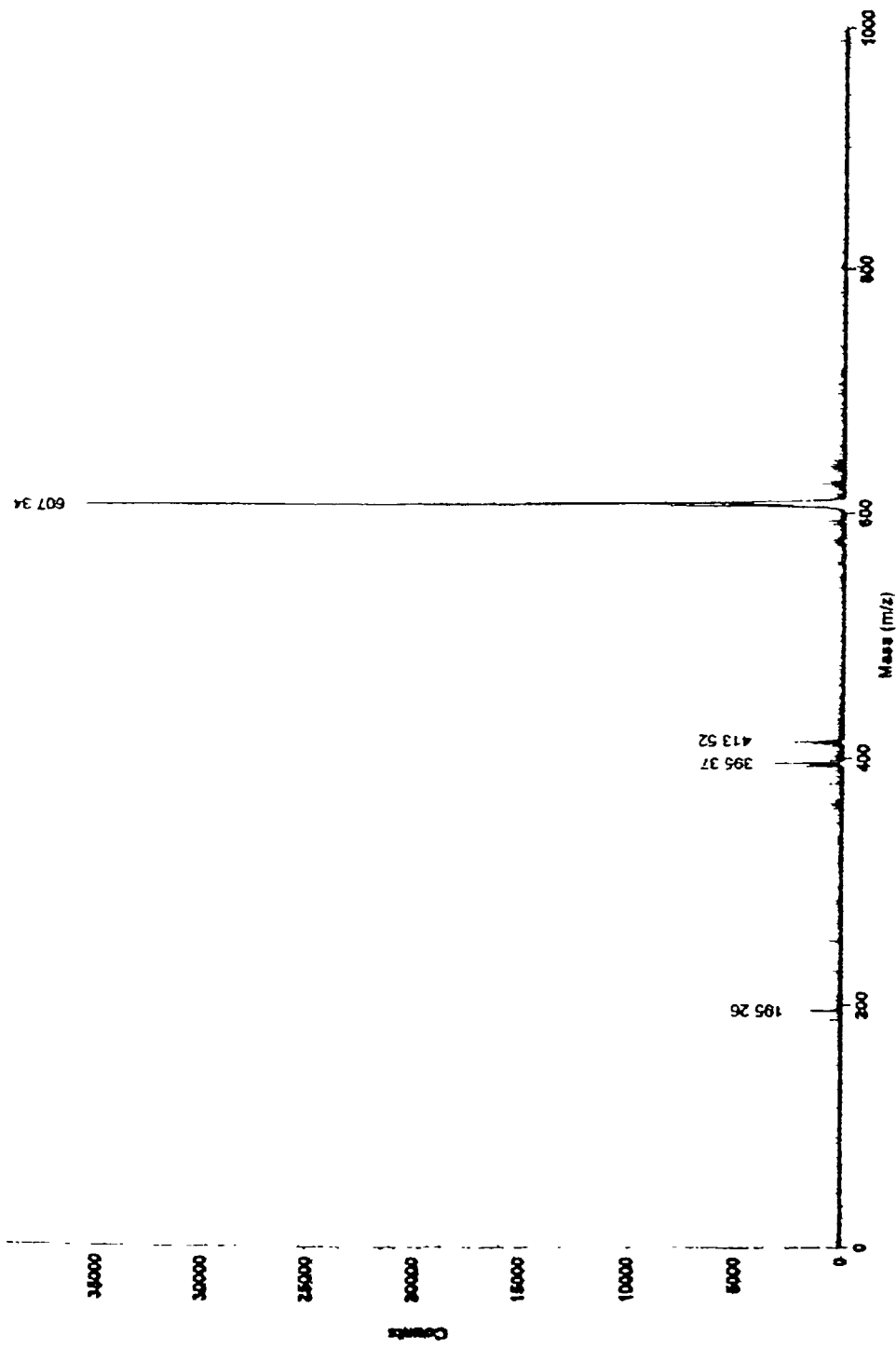
FIG. 7. Desorption ionization mass spectrum taken from the surface of the Carbon black—Halogenated acidic polymer film.

FIG. 7 is a graphic representation of a desorption ionization mass spectrum taken from the surface of a carbon black—halogenated acidic polymer film of the invention.

Absorption Layer

A necessary role that one or more layers, which may include the substrate, must play is the absorption of the incident photons and the conversion of this light into species-desorbing energy. The optical properties required by this absorption layer are determined by the electromagnetic energy (e.g., light) source used. For example, silicon makes an excellent absorber for an ultra-violet light source such as common nitrogen laser (wavelength of 337 nm), but may not work effectively with an infra-red source (depending on the wavelength) because of its optical bandgap structure. On the other hand, Ge will work for the shorter infra-red wavelengths. In general this absorber layer composition is selected to match the wavelength or wavelengths of the impinging electromagnetic radiation. Materials that can be used for this layer, with appropriate optical properties, include conductors, semiconductors, insulators, ceramics, polymers, organic materials, inorganic materials, or composites thereof. Proper choice of this layer can allow the electromagnetic energy source to be a variety of possibilities including light emitting diodes or lasers.

A micro-composite or nano-composite polymer film can also be used for this layer, which may include the substrate, in matrix-less photon desorption mass analysis devices or apparatuses. For example, a polymer including but not limited to, an acidic halogenated polymer, or mixtures of halogenated polymers, may be added to an inorganic or organic material, or combinations thereof. A preferred composite embodiment comprises a fluorinated, acidic polymer and carbon black. Composite polymer films or layers are conveniently prepared by mixing the selected organic polymer and inorganic/organic material (i.e., fluorinated acidic polymer and carbon black) in a suitable solvent; and thereafter forming a composite film from the mixture. The composite film may be formed by methods known in the art such as molding, casting, spin casting, spraying, and any combinations thereof. An advantage of using composite polymer films is that desirable properties of materials essential to laser desorption ionization are consolidated. For example, when a fluorinated, acidic polymer/amorphous carbon composite comprising carbon black particles embedded or suspended in the polymer matrix is used, carbon black particles efficiently absorb the laser energy and convert it to heat while the acidic polymer provides a means of holding the carbon particles together and can function to mediate proton transfer as a donating medium for the analyte. Modifying the polymer content or polymer chemistry also offers a means to control the surface energy of immobilization layer and therefore modify the adsorption, drying and crystallization of the analyte.

Immobilization Layer

The one or more necessary layers which are in contact with the sample atoms and/or molecules must hold the sample and allow it to effectively desorb and ionize, enabling it to interact with any ionizing/ionization enhancing agents if necessary. This layer may be composed of the same or similar material as the light coupling, thermal coupling, or absorption layer or may differ in both chemical composition and physical morphology. The morphology of this layer may range from solid, flat-surface (non-textured) material to high surface area to volume ratio very highly nano-textured material. The morphology of the film may be used to affect the mechanics and kinetics of analyte application, adsorption and concentration, and/or the adsorption and concentration of the ionizing and ionization enhancement agents. This affects signal properties, including but not limited to, sensitivity and resolution.

The chemical composition of this layer or layers can also affect signal response by modifying the interaction of the atomic and/or molecular species and other compounds with each other and the layer. Chemical composition of this layer may change species adsorption, desorption, ionization, conductivity and molecular affinity of the layer. The chemical composition of this layer may also affect its ability to be cleansed of noise (non-analyte) molecules during analyte positioning. The bulk and surface chemistries may be specifically tailored, by controlling layer processing (e.g., casting, deposition) chemistry or by post layer processing modification for controlling the aforementioned properties. We have demonstrated that hydrophobic or hydrophilic and acidic or basic surfaces influence analyte desorption and ionization by modifying analyte, ionizing agent and surface interaction. The reduction of van der Walls and hydrogen bonding via surface chemistry also may enhance analyte desorption/ionization. The immobilization layer or layers that are in contact with the sample atoms and/or molecules may be comprised of conductors, semiconductors, insulators, ceramics, polymers, organic materials, inorganic materials, or composites thereof.

This layer of the matrix-less devices of the present invention for photon desorption mass analysis may be a composite polymer containing film. The film may be either a micro-composite or a nano-composite film. Such composite polymer films include, but are not limited to, a suitable acidic halogenated polymer, or mixtures of acidic halogenated polymers, and a suitable organic or inorganic material, or combinations thereof. A preferred composite embodiment comprises acidic fluorinated polymer and the material carbon black.

Optical Coupling Layer

Another task that may be performed by one or more layers of the material system of this invention is coupling the incident light more effectively into the absorption layer. Several techniques can be used including optical impedance matching, anti-reflection coating, increasing the optical path length, and combinations thereof. Materials that can be used for this layer, with appropriate properties, include metals, semiconductors, insulators, ceramics, polymers, organic materials, inorganic materials, or composites thereof.

Substrate

For the material system of this invention, the substrate may play one or more of the roles mentioned above or simply serve as a support medium. The only necessary qualification of the substrate is that it must be compatible with the processing used to create subsequent layers. Materials that can be used for this layer include metals, semiconductors, insulators, ceramics, polymers, organic materials, inorganic materials, or composites thereof.

One or more of the different layers of the devices of the invention may be a conductor capable of being biased during the impingement of the desorbing light. Such layer biasing may be used to affect ionization of the analyte.

Processing Methods

The layers of these morphology tailored structures can come from grown or caste materials. They can be deposited films produced by a variety of methods including but not limited to the following: PVD such as sputtering, evaporation, and PEPLVD, CVD PECVD, ECR-PECVD, MOCVD electroplating, so-gel, tape casting, spin coating, nebulization, deposition, self-assembly, casting, liquid deposition, or assembly from liquid precursors, and any combinations thereof.

Composite polymer layers or films of the devices or apparatuses of the present invention may be prepared by methods known in the art. For example, organic polymers or polymers are mixed with organic or inorganic material or materials in a suitable solvent. A preferred organic polymer is a crosslinked halogenated acidic polymer. A preferred inorganic material is carbon black. The mixture is then formed into a film with removal of the solvent using methods known in the art such as molding, casting, spin casting, spray, and any combinations thereof.

Device Structure and Layer Organization

The layer options and requirements detailed above enable the material structures of this invention to be uniquely tailored for optimal performance based on the analytes, their sample preparation, the type of electromagnetic energy source used for desorption-ionization, the mass analysis technique and integration techniques. However, several basic rules apply to the overall device structure. These rules apply whether the electromagnetic energy enters through the immobilization layer holding the analyte (the front) or from the back. First, the impinging photons must be able to enter the absorber layer or layers of the device. Second, the immobilization layer must enable the desorbed analytes to have access to the mass detector.

Device Texturing and Patterning

Patterning of one or more of the layers in the device can serve many purposes. The localization of analytes, which is important for automation and sample delivery purposes, can be done on a macroscopic or microscopic scale with wells either pre-formed on the substrate or produced during subsequent film growth and processing. Furthermore, patterning of the immobilization layer via differences in hydrophobicity, hydrophilicity, chemical affinity, charge and polarity can localize and preferentially bind desired analytes. Patterning of a metallic grid on the immobilization layer can remove charge buildup during the desorbtion/ionization process in machines requiring a grounded stage. Finally, with the integration of these devices into micro-fluidic systems, patterning can be used to define the device location. Patterning can also be done by a variety of manufacturing techniques including pre-fabricated or molded substrates, self-assembly deposition, textured film growth, physical scribing, laser ablation and lithographic processes.

Patterning of one or more of the layers in the device can serve many purposes. The localization of analytes, which is important for automation and sample delivery purposes, can be done on a macroscopic or microscopic scale with wells either pre-formed on the substrate or produced during subsequent film growth and processing. Furthermore, patterning of the immobilization layer via differences in hydrophobicity, hydrophilicity, chemical affinity, charge and polarity can localize and preferentially bind desired analytes. Patterning of a metallic grid on the immobilization layer can remove charge buildup during the desorbtion/ionization process in machines requiring a grounded stage. Finally, with the integration of these devices into micro-fluidic systems, patterning can be used to define the device location. Patterning can also be done by a variety of manufacturing techniques including pre-fabricated or molded substrates, physical scribing, laser ablation and lithographic processes.

Photon Impingement Protocols

To extend the temporal duration or amount of analyte signal generation, it may be necessary to have the impinging photons execute a pattern in each given analyte-containing region. Such patterns would allow more analyte to be desorbed and may involve multiple paths across a given region. These protocols would be pre-programmed.

Chemical Additives

Chemical additives, which are allowed to interact with the analyte molecules during the desorption-ionization process, can act to enhance analyte detection. In order to increase the proportion of charged analyte species to neutrals, the surrounding environment can be made more acidic or basic. To create a more "soft" ionization process known molecules can be used with the analyte to act as a cooling media by which excess thermal energy may be transferred from the analyte during desorption. This greatly reduces the fragmentation of large molecules during mass analysis. Other chemical additives can act to condition or purify the surrounding media by chelating metal and salt ions known to reduce sensitivity and cause adducts. Hydrated molecules such as hygroscopic salts or other water containing molecules can provide a source of ions prior to or during desorbtion.

Finally, chemical additives such as surfactants and detergents can change the way analyte molecules and contaminates interact with each other and the immobilization layer surface. This can be useful in cleaning the surface during sample application, preventing agglomeration of analyte and preventing strong adherence of the analyte to the immobilization layer.

These chemical additives can be introduced into the process in the analyte preparation step, pre-coated on the immobilization layer, chemically attached to the immobilization layer, or introduced during desorption-ionization via fluidic or gaseous transport.

Mixed Phase Films

Matrix free desorption ionization mass spectrometry can also be mediated by mixed phase or composite material surfaces. In particular, when the desorbing/ionizing layer material is available in less expensive powder form, a cost effective approach is to form layers of this material from powder such that the particles are fixed in/by a resin material. The second ("glue") material may serve more than just fixing the particles together, it may also function as the radiation absorber and/or ionization enhancer. It is possible that the particles and the "glue" material may have completely distinct roles essential to desorption/ionization. For instance, the particle material may be a strong absorber while a poor ionization enhancer. In contrast, the second material may be a poor absorber but be or contain effective ionization enhancer(s). In one embodiment, the photon absorbing micro or nanoparticle can be, but is not limited to, a metal, organic, insulator, semiconductor or inorganic material. On the other hand, the superior properties of the two materials (radiation absorption and ionization enhancement) can be brought together in a composite by mixing them. In this way a superior desorbing/ionizing layer can be obtained. The composite layer could be comprised of more than two materials (either in particulate or glue form) to better tailor its superior desorbing/ionizing properties. A low cost method of making a composite film is mixing its components in a liquid solvent, and then placing the liquid mixture onto a substrate (e.g., casting, spinning, spray, brush, dipping, printing etc. techniques).

Figure 2:
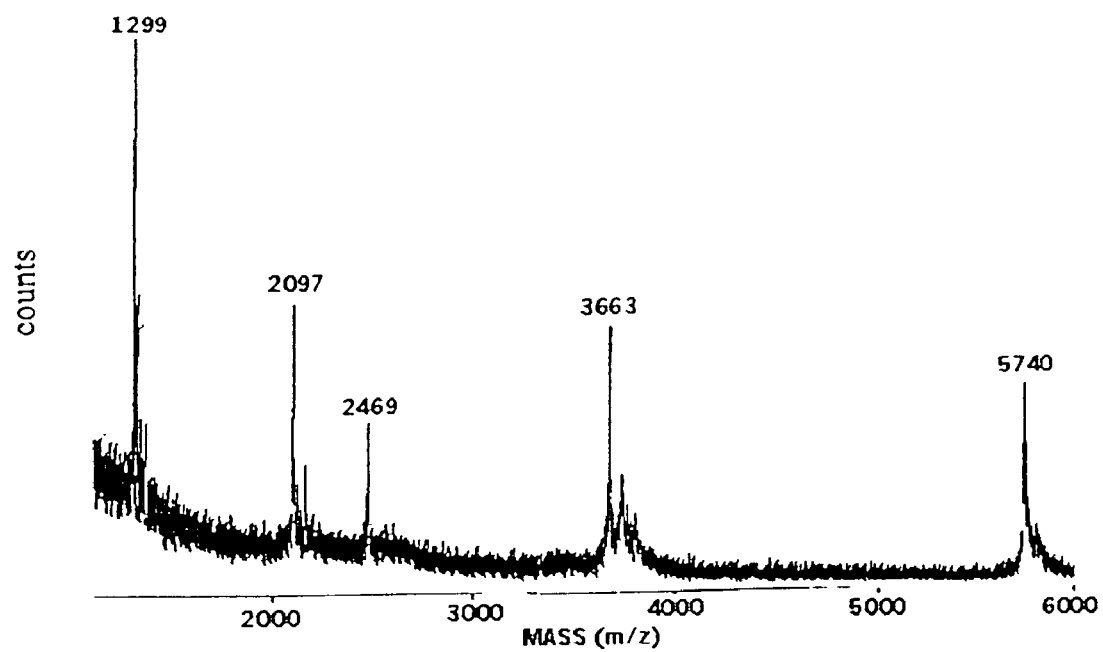
FIG. 2 is a mass spectrum obtained using a silicon dioxide layer on top of silicon.

As a specific example, amorphous carbon—halogenated acidic polymer composite films were prepared by spin casting. The carbon black produced from acetylene with an average particle size of 0.042 µm. The Halogenated acidic polymer solution with 5.0–5.4% polymer content by weight was purchased from DuPont. Carbon black was mixed into the Halogenated acidic polymer solution to an equal amount of polymer by weight. The mixture was ultrasonicated for 6 h and stirred for 12 h before spun on 1"×1" Corning 1737 glass substrates. A uniform film thickness of 1.8 µm was obtained at a spin rate of 2000 rpm in 40 s. The spin on was followed by a 120° C. thermal anneal for 15 minutes. The resultant film was found to be a very efficient light absorber in the visible and UV range as seen from its exceptionally low reflectance and transmission characteristics in FIG. 6. This is simply attributed to amorphous carbon's being a very efficient light absorber. On the other hand, the role of Halogenated acidic polymer other than being a resin could be ionization enhancement. This is because Halogenated acidic polymer, a perfluorosulfonic acid/tetrafluoroethylene copolymer in the acid ($H^+$) form, is well known for its being an efficient proton storage, transport and exchange properties. The conductivity of the film was measured to be about 1.6 S/cm using glass substrates with coplanar metal contacts. FIG. 2 depicts a desorption ionization mass spectrum taken from the surface of the Carbon black—Halogenated acidic polymer film after a 1.0 ng reserpine was dried from a droplet on the surface. It is evident from FIG. 7 that a very clear analyte signal is obtainable.

Integration with Preparation and Application Devices.

The deposited devices and mass analysis technique of this invention have the unique ability to be integrated with a large number of sample delivery and preparation techniques plus a large number of mass analyzers. Preparation of the analyte molecules can be as simple as placing a drop of the molecules on the immobilization layer surface and allowing them to dry. It is also possible to allow the analyte molecules to adsorb to the immobilization layer surface out of a gaseous or liquid solution. This simple fluid handling can be performed by a number of automated, high throughput handling systems. More complex schemes include the use of micro-fluidic, on chip, system that perform chromatography or purification. The deposited systems of this invention can be easily used in tandem with a chip-based system or integrated into the micro-fluidic device. The use of an integrated micro-fluidic system can also be used to deliver desorption-ionization enhancing agents to the analyte during mass analysis in order to prolong detection signal.

Many mass spectrometry techniques can be used to analyze the desorbed-ionized species. These may include but are not limited to: time of flight, quadrapole, ion trap, plasmon resonance or combinations thereof.

The present invention comprises a class of morphology-tailored structures (or material systems) for the mass analysis and a method of analysis of atoms, molecules and molecular compounds and complex structures such as adhered cells when coupled with light desorption-ionization mass spectrometry. These material systems act to hold analytes and allow them to desorb and ionize in the presence of light without the traditional organic or non-organic matrix. A schematic of the difference between traditional MALDI and the technique of this invention is given in FIG. 1. The material systems of this invention are composed of one or more layers and a substrate to which they are adhered. The critical roles of adsorption, analyte immobilization, optical coupling, and substrate may be played by one or more material layers. one or more of these layers may be biased during photon exposure to influence desorption. The specifics of layer function and formation are detailed below.

Absorption layer.

Figure 3:
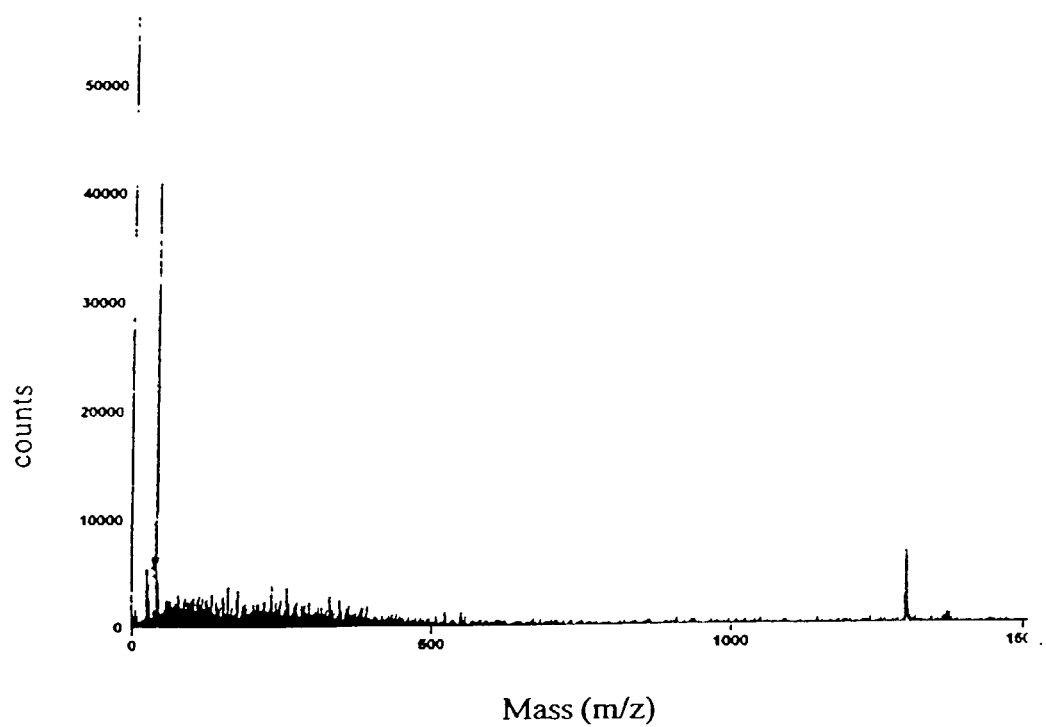
FIG. 3 is a mass spectrum obtained using a deposited germanium thin film.

A necessary role that one or more layers, which may include the substrate, must play is the absorption of incident photons from the light source. The light source may range from IR to UV wavelengths and from coherent and in phase (laser) to non-coherent. The choices of light source and absorber material are dependent on each other. The absorber must be able to absorb enough of the incident light to provide sufficient thermal energy to desorb the analytes from the immobilization layer, which may or may not be the absorber layer itself. The high light adsorption coefficients of semiconductor materials make the use low cost, light emitting diodes as a light source an attractive option, when compared to the traditional UV laser sources that are necessary for MALDI. A specific embodiment of this invention is the use of a 337 nm UV light source and Si or Ge based absorber materials. These two materials, in amorphous through crystalline phases, absorb UV light very efficiently, and we have demonstrated this in FIGS. 2 and 3. This idea can easily be extrapolated to include all semiconductors in the binary, tertiary, mixed, and graded varieties. All other materials for use as an absorber, with appropriate optical properties are encompassed by the scope of this invention including: metals, semiconductors, insulators, ceramics, polymers, organic materials or composites thereof.

The only requirement of the position of the absorber layer in the material system of this invention is that the incident photons have access to this layer. A unique aspect of this invention is the ability to illuminate the device from any direction including through the substrate (rear of the device) and through the immobilization layer (front of the device). This is important if the analytes adsorb the light wavelengths used for desorption and ionization. For instance small molecules, peptides and proteins adsorb UV wavelengths efficiently, which can lead to thermal degradation and fragmentation of the analyte, reducing the sensitivity of detection. Unlike MALDI, in our system the analyte is not required to sit in the photon path, thus entirely avoiding any photon/analyte interactions.

Immobilization Layer.

One or more layers in the material system of this invention must come into contact with the sample atoms/and or molecules. This layer must hold the sample and allow it to effectively desorb and ionize in the presence of the energy generated by light adsorption in absorber layer, which may also act the immobilization layer. The material properties required of the immobilization layer range widely and depend highly on its interaction with the sample species. Also, if the immobilization layer is in the light path between the light source and the absorber layer, it must have optical properties such that incident photons are allowed to reach the absorber. Specific materials of this invention used for the immobilization layer include but are not limited to silicon, germanium, silicon dioxide, germanium oxide, indium, gallium, cadmium, selenium, tellurium, and their alloyed forms. All other materials for use as an immobilization layer, with appropriate material properties are encompassed by the scope of this invention including: metals, semiconductors, insulators, ceramics, polymers, organic materials or composites thereof.

A. Morphology of the Immoblization Layer

The morphology and physical structure of this layer can be tailored for specific applications. Three morphological structures of the immobilization layer, specific to this invention, include nanometer range texturing, micrometer range texturing, and a macro-scale flat surface. The first two types of films we categorize as discontinuous films. The macro-scale film is what we term a continuous film. The advantages and disadvantages of these three film structures are given in Table 1. The immobilization layer may be comprised of one or more of these morphological features.

TABLE 1

Morphological structures of the immobilization layer of this invention and their advantages and disadvantages

| Morphology | Properties | Advantages | Possible Disadvantages | Examples |
|---|---|---|---|---|
| Nanometer scale texture | Ultra high surface area<br>High steric interaction with molecular species<br>Strong capillary forces | Very high loading capacity of analyte<br>High adsorption of analyte species from wet or dry ambient<br>Excellent | High adsorption of ambient noise | Nanoscale deposited column/void network material |

TABLE 1-continued

Morphological structures of the immobilization layer of this invention and their advantages and disadvantages

| Morph-ology | Properties | Advantages | Possible Disadvantages | Examples |
|---|---|---|---|---|
| Micrometer scale texture | High surface area | uniformity of analyte coverage High loading capacity of analyte Low adsorption of ambient noise | films | glancing angle deposited |
| Flat surface | Low surface area | Very low adsorption of ambient noise | Poor uniformity of analyte coverage Low sample loading density | Evaporated, spun-on, or sputtered materials |

B. Chemical Modifications and Additives to the Immobilization Layer

The surface and bulk chemistry of this layer can also be tailored during layer processing or post layer processing for specific interactions with the analyte molecules, desorption/ionization enhancing species, and the immobilization layer surface. For example, for deposited layers the chemistry of the film can be modified by plasma, thermal or wet chemistries such as, but not limited to; RIE, CVD, PECVD, DVD, MOCVD, PVD and wet chemical modification. A specific embodiment of this invention is to use surface chemical modifications either during or after film deposition to control hydrophobicity and hydrophylicity of the film, such as the incorporation of carbon and fluorine while depositing a film or the growth of a thermal oxide. The chemistry of the immobilization layer can be tailored for certain molecules to improve their desorption and ionization efficiency. Other functional groups can also be used to tailor the interaction of the surface with the analyte molecules by altering hydrogen bonding, surface charge, van Der Walls interaction, polar and non-polar interactions, steric interaction, antigen/antibody reactions etc. The surface chemistry and energy can play a critical role in the manner an analyte interacts with the surface during adsorbtion. The manner in which a analyte crystallizes can play a large role in the efficiency with which it desorbs and ionizes. As an example, composite halogenated, acidic polymers provide an excellent surface for analyte crystallization, while the acidic groups provide a source of ions for the ionization process. Crosslinked polymers are a more thermally stable surface that provides spectrums with very little noise from polymeric breakdown. Carbon black/halogenated polymer composites possess an extremely hydrophobic surface composition, when compared to the hydrophobicity of the polymer surface alone. The water contact angle of these materials are in excess of 100 degrees.

Other chemical additives specifically enhance the ionization of the analyte molecules. The additives can be chemically bonded to the surface prior to analyte application, applied to the surface in solid liquid or gas phase, or applied into the analyte solution prior or during mass analysis. In order to improve ionization efficiency, a number of materials, including but not limited to additives that are salts, hydrated molecules, surfactants, detergents, chelators, acids and bases, may be added on the surface of the apparatus and dried prior to the addition of the analyte, or added to the analyte prior to or during contacting the analyte to the apparatus. A specific chemical modification for improving ionization efficiency is the control of surface pH to enhance either negative or positive ion spectra. For example this can be accomplished simply by allowing HCl or Trifluoroacetic acid (TFA) to dry on the immobilization layer prior to applying the analyte or attaching and acid or basic group to the immobilization layer surface using a silanization reaction. Hydrated salts such as $MgCl_2$ can provide a signifigant source of protons in a crystallized analyte for ionization. Chelating agents such as ammonium citrate remove salt ions which form adducts during mass analysis and also disperse analytes for more uniform spatial distribution. Other small molecules added to the analyte, such as amino acids interact with the analyte in the desorption plume and adsorb energy from the analyte reducing fragmentation during mass analysis. HCl and TFA may also be added to the analyte.

Another useful chemical modification can act to self-clean the device during sample application. By using a layer composition or thin surface coating that is soluble in the sample solvent, the coating will be dissolved, "cleaning" the surface of adhered contaminates such as hydrocarbons. A specific embodiment of this invention is the use of a water-soluble germanium oxide for its self-cleaning properties. Such an oxide will be inherently present as soon as Ge is exposed to atmosphere. This nascent oxide may be augmented by oxide formed in situ by wet chemistry, thermal or plasma oxidation or deposited as a thin film by the deposition methods previously mentioned.

Optical coupling layer.

Figure 4:
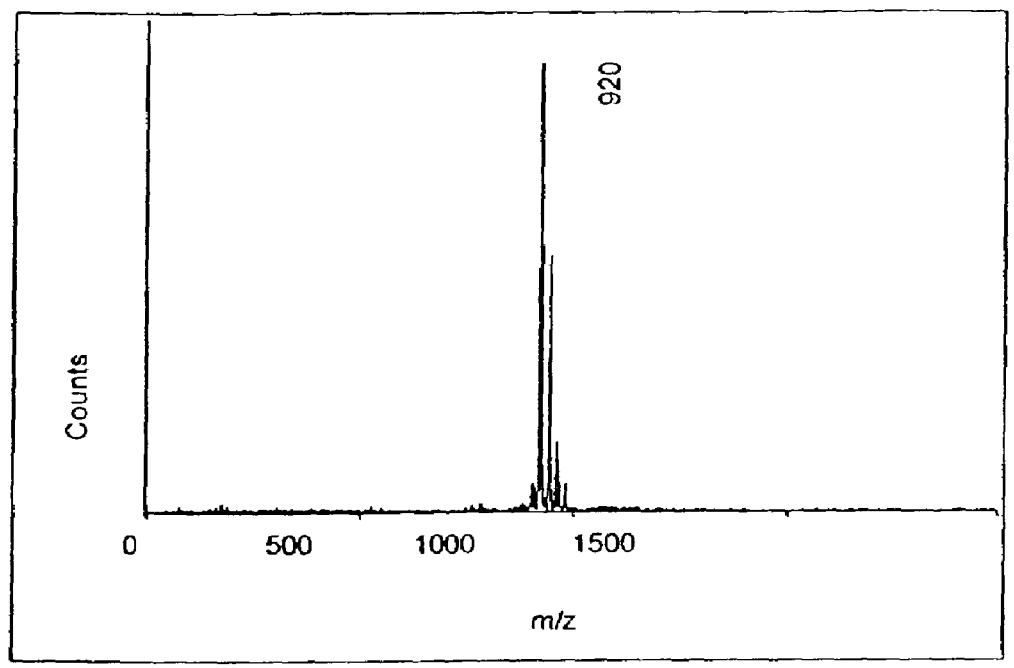
FIG. 4 is a mass spectrum obtained using a high surface to volume silicon material.

Another task that may be performed by one or more layers of the material system of this invention is coupling the incident electromagnetic radiation more effectively into the absorption layer. Several techniques can be used, such as those used modern solar cell devices, including but not limited to, optical impedance matching, anti-reflection coating, increasing the optical path length, and combinations thereof. Specific techniques demonstrated in FIGS. 2 and 4 include using silicon dioxide for an anti reflection coating and to serve as an immobilization layer, and using nanostructured silicon to act as an optical impedance matching medium as well as an absorber. Materials that can be used for this layer, with appropriate properties, include metals, semiconductors, insulators, ceramics, polymers, organic materials, or composites thereof.

Substrate.

For the material system of this invention, the substrate to which the layers are adhered onto may play one or more of the roles mentioned above or simply serve as a support media. The only necessary qualification of the substrate is that it must be compatible with subsequent processing. The substrate may also be pre-patterned for sample preparation and localization. Specific embodiments demonstrated in this invention use inexpensive acrylic, and polyimide plastics, glasses and metal foils as substrates. In general, materials that can be used for this layer include metals, semiconductors, insulators, ceramics, polymers, organic materials, or composites thereof.

Deposition Methods.

Deposited films were preferably used to demonstrate this invention. Such deposited films can be deposited by a variety of methods including but not limited to the following: PVD such as sputtering and evaporation, CVD, PECVD, ECR-PECVD, PEPVD, electroplating, sol-gel, tape casting, self-assembly, liquid deposition, nebulization deposition, and spin coating. Specific techniques of the present invention include evaporation, sputtering, PECVD, and combinations thereof. Films or layers of the present invention are not limited to deposited films.

It is understood that certain films, i.e., polymer composite films, that are suitable for matrix-free photon desorption mass analysis devices of the present invention are not required to be deposited. For example, micro-composite or nano-composite polymers films presented herein may be used. They can be prepared by processing methods known in the art such as mixing organic polymer(s) and inorganic materials(s) in a solvent, and thereafter forming a composite film from the mixture. Such composite films may be prepared, for example, by molding, casting, spin casting, spraying, and any combinations thereof, or other procedures known to produce such polymer composites.

Device Texturing and Patterning.

The texturing of one or more layers in the device of this invention can have several effects. Texturing of a reflective layer behind the absorber (on the opposite side of the device from the light source), increases the optical path length and enhances optical absorption in thin absorber layers. Texturing of the immobilization layer can have various effects depending on the length scale considered. As shown in Table 1 above, micro-scale roughness allows more analyte and desorption-ionization enhancing agents to be present per incident laser area. This can increase the sensitivity and longevity of analyte signal. On the nano-scale, the surface roughness will not only enhance signal sensitivity and longevity, but may also act to enhance light coupling into the absorber by impedance matching. The nanoscale texturing also allows effective adsorption of analytes from the gas or liquid phase and provides better uniformity of the analyte distribution for more reproducible signal than achieved using other morphologies. Texturing can be done by a variety of manufacturing techniques including pre-fabricated or molded substrates, physical roughening, laser ablation, lithographic processes, and textured film growth. Methods of textured film growth of this invention include nano-structured PE-CVD growth conditions, zone growth model surface texturing, and glancing angle deposition.

Patterning of one or more of the layers in the device can serve many purposes. The localization of analytes, which is important for automation and sample delivery purposes, can be done on a macroscopic or microscopic scale with wells either pre-formed on the substrate or produced during subsequent film growth and processing. For instance wells could be hot embossed into a plastic substrate. Localization could also be attained by the plasma deposition of polymers or by the selective removal of an oxide layer. It could be attained by using "soft" lithographic patterning, such as PDMS stamping of molecules. Furthermore, patterning of the immobilization layer to causes differences in hydrophobicity, chemical affinity, acidity, charge and polarity can localize and preferentially bind desired analytes. Patterning of a metallic grid on the immobilization layer can remove charge buildup during the desorbtion/ionization process in machines requiring a grounded stage. Finally, with the integration of these devices into micro-fluidic systems, patterning can be used to place the devices where needed. Patterning can also be done by a variety of manufacturing techniques including pre-fabricated or molded substrates, physical scribing, stamping, embossing, laser ablation and lithographic processes.

Integration with Preparation, Application, and Analysis Devices.

The deposited devices and mass analysis technique of this invention have the unique ability to be integrated with a large number of sample delivery and preparation techniques plus a large number of mass analyzers. Preparation of the analyte can be as simple as placing a drop of the molecules on the immobilization layer surface and allowing it to dry. It is also possible to allow the analyte to adsorb to the immobilization layer surface out of a gaseous or liquid solution. This simple gas or fluid handling can be performed by a number of automated, high throughput sampling systems. More complex schemes include the use of computer integrated micro-fluidic, on chip, systems that perform chromatography or purification. The deposited systems of this invention can be easily used in tandem with a chip-based system or integrated into the micro-fluidic device. The use of an integrated micro-fluidic system can also be used to deliver desorption-ionization enhancing agents, such as water, to the analyte during mass analysis in order to prolong detection signal.

Many mass spectroscopic methods can be used to analyze the desorbed-ionized species. These may include but are not limited to: time of flight, quadrapole, ion trap, plasmon resonance or combinations thereof.

Device Structure and Layer Organization.

The layer options and requirements detailed above enable the morphology-tailored material structures of this invention to be uniquely designed for optimal performance based on the analytes, their sample preparation, the type of electromagnetic source used for desorption-ionization, the mass analysis technique used and integration techniques employed. However, there are basic rules that apply to the overall device structure. First, the impinging photons must be able to enter the absorber layer or layers of the device. Second, the immobilization layer must enable the desorbed analytes to enter the necessary mass detection area. FIG. 5 provides a variety of specific device structures unique to this invention.

Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the following claims.

What is claimed is:

1. An apparatus for providing an ionized analyte for mass analysis by photon desorption comprising:
   at least one layer for contacting an analyte; and
   a substrate on which said layer is deposited, wherein said analyte upon irradiation of said apparatus with a photon source desorbs and ionizes for mass analysis;
   wherein said layer is an analyte immobilization and an anti-reflection coating layer or an optical impedance marching and an absorber layer.

2. The apparatus of claim 1, further comprising one or more layers deposited on said substrate that act to absorb and convert photons to energy sufficient to desorb and ionize said analyte.

3. The apparatus of claim 2, wherein said at least one layer is selected from at least one of the group consisting of metals, semiconductors, insulators, ceramics, polymers, organic materials, and inorganic materials.

4. The apparatus of claim 2, wherein said layer is deposited by at least one of the methods selected from the group consisting of physical vapor deposition, chemical vapor deposition, liquid deposition, molecular beam epitaxy, plasma assisted chemical vapor deposition, sol-gels, nebulization, spraying, electroplating, tape casting, spin coating, assembly from liquid chemical precursors, printing, and self-assembly.

5. The apparatus of claim 2, wherein one or more of said deposited layers is a continuous film, or a discontinuous film.

6. The apparatus of claim 2, wherein the thickness of said layer is essentially uniform from 5 nm to 10 microns.

7. The apparatus of claim 1, wherein said substrate upon irradiation absorbs and converts photon energy to energy sufficient to desorb and ionize said analyte.

8. The apparatus of claim 1, wherein said substrate is selected from at least one of the group consisting of metals, semiconductors, insulators, ceramics, polymers, organic materials, and inorganic materials.

9. The apparatus of claim 1, wherein said deposited layer contacting said analyte is selected from at least one of the group consisting of silicon, silicon dioxide, germanium, germanium oxide, indium, gallium, cadmium, selenium, tellurium, and alloys and compounds thereof, carbon, hydrogen, semiconductors, insulators, metals, ceramics, polymers, other inorganic material, and organic material.

10. The apparatus of claim 1, wherein said layer is deposited by at least one of the methods selected from the group consisting of physical vapor deposition, chemical vapor deposition, liquid deposition, molecular beam epitaxy, plasma assisted chemical vapor deposition, sol-gels, nebulization, spraying, electroplating, rape casting, spin coating, assembly from liquid chemical precursors, printing, and self-assembly.

11. The apparatus of claim 1, wherein said deposited layer is a continuous film, or a discontinuous film.

12. The apparatus of claim 1, wherein said layer contacting said analyte is physically or chemically modified, surface functionalized, or patterned.

13. The apparatus of claim 11, wherein the surface of said layer is chemically modified to control acid behavior, basic behavior, hydrophobicity, or hydrophylicity.

14. The apparatus of claim 1, wherein the thickness of said layer is essentially uniform from 5 nm to 10 microns.

15. The apparatus of claim 1, wherein said layer contacting an analyte is patterned by at least one method selected from the group consisting of non-textured, micro-scale textured, and nano-scale texturing.

16. The apparatus of claim 1, wherein the analyte is in an amount greater than 1 attomole.

17. The apparatus of claim 1, further comprising a microfluidic apparatus, a nano-fluidic apparatus, or combination thereof.

18. The apparatus of claim 1, further comprising a mass spectrometer for analysis of the mass of said analyte.

19. The apparatus of claim 18, wherein said mass analysis is by at least one apparatus selected from the group consisting of time of flight mass spectrometer, quadrapole mass spectrometer, and ion trap device.

20. The apparatus of claim 1, wherein one or more of said contacting layers is physically or chemically modified, surface functionalized, or patterned.

21. The apparatus of claim 20, wherein the surface of said layer is chemically modified by at least one method to control acid behavior, basic behavior, water content, hydrophobicity or hydrophylicity.

22. The apparatus of claim 1, wherein said layer contacting an analyte is selected from at least one of the group consisting of a non-textured, a micro-scale textured layer, and a nano-scale textured layer.

23. The apparatus of claim 1, wherein the analyte is in an amount less than 1 attomole.

24. The apparatus of claim 1, further comprising at least one of a micro-fluidic apparatus, or a nano-fluidic apparatus.

25. The apparatus of claim 1, further comprising a device for analysis of the mass of said analyte.

26. The apparatus of claim 25, wherein said device is at least one apparatus selected from the group consisting of time of flight mass spectrometer, quadrapole mass spectrometer, and ion trap device.

27. A method for providing an ionized analyte for analysis of mass comprising:
providing an apparatus comprising at least one layer for contacting an analyte wherein said layer is deposited on a substrate; wherein the at least one layer is an analyte immobilization and an anti-reflection coating layer or an optical impedance matching and an absorber layer;
contacting an amount of an analyte containing entities whose mass or masses are to be determined with said deposited layer;
and irradiating said apparatus to desorb and ionize said analyte.

28. The method of claim 27, wherein said analyte is substantially free of a matrix.

29. The method of claim 27, wherein said analyte is selected from at least one of the group comprising organic chemical compositions, inorganic chemical compositions, biochemical compositions, cells, micro-organisms, peptides, polypeptides, proteins, lipids, carbohydrates, drug candidate molecules, drug molecules, drug metabolites, combinatorial chemistry products, and nucleic acids.

30. The method of claim 27, wherein said apparatus further comprises one or more layers deposited on said substrate that upon irradiating said apparatus absorb and convert photon energy sufficient to desorb and ionize said analyte.

31. The method of claim 30, wherein said one or more layers is selected form at least one of the group consisting of metals, semiconductors, insulators, ceramics, polymers, organic materials, and inorganic materials.

32. The method of claim 30, wherein said one or more layers is deposited by at least one of the methods selected from the group consisting of physical vapor deposition, chemical vapor deposition, liquid deposition, molecular beam epitaxy, plasma assisted chemical vapor deposition, sol-gels, nebulization, spraying, electroplating, tape casting, spin coating, assembly from liquid chemical precursors, printing, and self-assembly.

33. The method of claim 27, wherein said substrate upon irradiation of said apparatus absorbs and converts photons to energy sufficient to desorb and ionize said analyte.

34. The method of claim 27, wherein said substrate is selected from at least one of the group consisting of metals, semiconductors, insulators, ceramics, polymers, organic materials, and inorganic materials.

35. The method of claim 27, wherein said deposited layer contacting said analyte is selected form at least one of the group consisting of silicon, silicon dioxide, germanium, germanium oxide, indium, gallium, cadmium, selenium, tellurium, and alloys and compounds thereof, carbon, hydrogen, semiconductors, insulators, metals, ceramics, polymers, other inorganic material, and organic material.

36. The method of claim 27, wherein said deposited layer of said apparatus is deposited by at least one of the methods selected from the group consisting of physical vapor deposition, chemical vapor deposition, liquid deposition, molecular beam epitaxy, plasma assisted chemical vapor deposition, sol-gels, nebulization, spraying, electroplating, tape casting, spin coating, assembly from liquid chemical precursors, printing, and self-assembly.

37. The method of claim 27, wherein said deposited layer of said apparatus contacting said analyte is a continuous film or a discontinuous film.

38. The method of claim 27, wherein said deposited layer of said apparatus contacting said analyte is physically or chemically modified, surface functionalized, or patterned.

39. The method of claim 27, wherein said layer contacting said analyte is at least one of non-textured, micro-scale textured, or nano-scale textured.

40. The method of claim 39, wherein said layer is textured by at least one of method selected from the group comprising prefabricating textured substrates, physical roughening, laser ablation, lithographic processes, textured film growth, and self-assembly deposition.

41. The method of claim 27, wherein said analyte is in an amount less than 1 attomole.

42. The method of claim 27, wherein the thickness of said layer is essentially uniform from 5 am to 10 microns.

43. The method of claim 27, further comprising adding an enhancing agent to said analyte prior to irradiating said apparatus.

44. The method of claim 43, wherein said enhancing agent is at least one agent selected from the group comprising ammonium citrate, HCl, TFA, salts, hydrated molecules, surfactants, detergents, acids, and bases.

45. The method of claim 27, wherein said apparatus further comprises at least one apparatus selected from the group consisting of a micro-fluidic apparatus, and a nano-fluidic apparatus.

46. The method of claim 27, further comprising analyzing the mass of said ionized analyte by a device.

47. The method of claim 46, wherein said analyzing the mass of said ionized analyte is by at least one of method selected from the group comprising time of flight mass spectroscopy, quadrapole mass spectroscopy, and by utilizing an ion trap device.

48. A method for providing an ionized analyte for analysis of mass comprising:
providing an apparatus comprising at least one layer for contacting an analyte wherein said layer is deposited on a substrate;
contacting an amount of the analyte containing entities such as molecules whose mass or masses are to be determined with said deposited layer; and
irradiating said apparatus to desorb and ionize the analyte;
wherein said layer is chemically modified to control hydrophobicity or hydropilicity.

49. A method for providing an ionized analyte for analysis of mass comprising:
providing an apparatus comprising at least one layer for contacting an analyte wherein said layer is deposited on a substrate;
contacting an amount of the analyte containing entities such as molecules whose mass or masses are to be determined with said deposited layer; and
irradiating said apparatus to desorb and ionize the analyte;
wherein said layer is chemically modified to control the surface pH of said layer.

50. A method for determining a physical property of an analyte component comprising the steps of:

providing an apparatus comprising at least one layer for contacting the analyte and a substrate on which the layer is deposited;
positioning an amount of the analyte on the layer used for contacting the analyte;
irradiating the apparatus having the contacted analyte;
desorbing and ionizing at least one component of the analyte; and
analyzing the at least one ionized component of the analyte for a physical property;
wherein said layer is chemically modified to control hydrophobicity or hydrophilicity.

51. A method for determining a physical property of an analyte component comprising the steps of:
providing an apparatus comprising at least one layer for contacting an analyte and a substrate on which the layer is deposited;
positioning an amount of an analyte on the layer used for contacting the analyte;
irradiating the apparatus having the contacted analyte;
desorbing and ionizing at least one component of the analyte; and
analyzing the at least one ionized component of the analyte for a physical property;
wherein said layer is chemically modified to control the surface pH of said layer.

52. An apparatus for providing an ionized analyte for mass analysis by photon desorption comprising:
at least one layer for contacting an analyte; and
a substrate on which said layer is deposited,
wherein said analyte upon irradiation of said apparatus with a photon source desorbs and ionizes for mass analysis;
said deposited layer being a composite material comprising an organic material and a photon adsorbing micro or nanoparticle.

53. A device of claim 52 where the organic material is polymer.

54. A device of claim 53 where the polymer is a halogenated material.

55. A device of claim 54 where the polymer is an acid.

56. A device of claim 53 wherein the polymer is a fluorinated/sulfur containing material.

57. A device of claim 52 where the photon adsorbing micro or nanoparticle is a semiconductor.

58. A device of claim 52 where the photon adsorbing micro or nanoparticle is a metal, organic, insulator or inorganic material.

59. A device of claim 52 where the photon adsorbing micro or nanoparticle is carbon.

60. An apparatus for providing an ionized analyte for mass analysis by photon desorption comprising:
at least one layer for contacting an analyte, said layer being an analyte immobilization and an anti-reflective coating layer; and
a substrate on which said layer is deposited;
wherein, upon irradiation of said apparatus with a photon source, the analyte desorbs and ionizes for mass analysis.

61. The apparatus of claim 60 further comprising one or more layers deposited on said substrate that act to absorb and convert photons to energy sufficient to desorb and ionize the analyte.

62. The apparatus of claim 60 wherein said deposited layer contacting said analyte comprises silicon dioxide.

63. A method for providing an ionized analyte for analysis of mass comprising the steps of:

providing an apparatus comprising at least one layer for contacting an analyte wherein said layer is deposited on a substrate, said layer being an analyte immobilization and an anti-reflective coating layer;

contacting an amount of the analyte with said deposited layer, the analyte containing entities such as molecules whose mass or masses are to be determined; and, irradiating said apparatus to desorb and ionize the analyte.

64. An apparatus for providing an ionized analyte for mass analysis by photon desorption comprising:

at least one layer for contacting an analyte, said layer being an optical impedance matching arid an absorber layer; and a substrate on which said layer is deposited;

wherein, upon irradiation of said apparatus with a photon source, the analyte desorbs and ionizes for mass analysis.

65. The apparatus of claim 64 wherein said deposited layer contacting said analyte is selected from at least one of the group consisting of silicon, silicon dioxide, semiconductors, insulators, metals, ceramics, polymers, and organic material.

66. The apparatus of claim 65 wherein said deposited layer contacting the analyte comprises nanostructured silicon.

67. A method for providing an ionized analyte for analysis of mass comprising the steps of:

providing an apparatus comprising at least one layer for contacting an analyte wherein said layer is deposited on a substrate, said layer being an optical impedance matching and an absorber layer;

contacting an amount of the analyte with said deposited layer, the analyte containing entities such as molecules whose mass or masses are to he determined; and, irradiating said apparatus to desorb and ionize the analyte.

* * * * *